US012654036B2

(12) United States Patent
Shabtay et al.

(10) Patent No.: US 12,654,036 B2
(45) Date of Patent: Jun. 16, 2026

(54) METHOD FOR TREATING HEART FAILURE BY IMPROVING EJECTION FRACTION OF A PATIENT

(71) Applicant: SONIVIE LTD., Rosh Haayin (IL)

(72) Inventors: Or Shabtay, Kibbutz Farod (IL); Dalit Shav, Rehovot (IL)

(73) Assignee: SONIVIE LTD., Rosh Haayin (IL)

( * ) Notice: Subject to any disclaimer, the term of this patent is extended or adjusted under 35 U.S.C. 154(b) by 1322 days.

(21) Appl. No.: 16/495,177

(22) PCT Filed: Mar. 20, 2018

(86) PCT No.: PCT/IL2018/050316
§ 371 (c)(1),
(2) Date: Sep. 18, 2019

(87) PCT Pub. No.: WO2018/173047
PCT Pub. Date: Sep. 27, 2018

(65) Prior Publication Data
US 2020/0094080 A1 Mar. 26, 2020

Related U.S. Application Data

(60) Provisional application No. 62/473,532, filed on Mar. 20, 2017, provisional application No. 62/473,512, filed on Mar. 20, 2017, provisional application No. 62/473,545, filed on Mar. 20, 2017.

(51) Int. Cl.
*A61N 7/00* (2006.01)
*A61B 5/055* (2006.01)
(Continued)

(52) U.S. Cl.
CPC ................ *A61N 7/00* (2013.01); *A61B 18/00* (2013.01); *A61B 18/0206* (2013.01);
(Continued)

(58) Field of Classification Search
None
See application file for complete search history.

(56) References Cited

U.S. PATENT DOCUMENTS 6,740,648 B2 5/2004 Ghazzi et al.
6,970,742 B2 11/2005 Mann et al.
(Continued)

FOREIGN PATENT DOCUMENTS

WO 2015193889 12/2015
WO 2016084081 6/2016
WO 2016084081 A1 6/2016

OTHER PUBLICATIONS

Leopold, J. A. (2015). Catheter-based therapies for patients with medication-refractory pulmonary arterial hypertension. Circulation: Cardiovascular Interventions, 8(11). https://doi.org/10.1161/circinterventions.115.003332 (Year: 2015).*
(Continued)

*Primary Examiner* — Charles A Marmor, II
*Assistant Examiner* — Marc D. Honrath
(74) *Attorney, Agent, or Firm* — Seager, Tufte & Wickhem, LLP

(57) ABSTRACT

A method for improving an ejection fraction of a patient in need thereof, including positioning a pulmonary artery manipulation device in a target blood vessel, within the pulmonary vasculature of the patient; and impairing the activity of at least one sympathetic nerve, nerve fiber or neuron, using the pulmonary artery manipulation device, to denervate the target blood vessel, thereby improving the ejection fraction of the patient.

11 Claims, 4 Drawing Sheets

100

110 — POSITIONING A PULMONARY ARTERY MANIPULATION DEVICE WITHIN OR IN PROXIMITY TO A TARGET BLOOD VESSEL, WITHIN THE PULMONARY VASCULATURE OF A PATIENT HAVING A REDUCED EJECTION FRACTION

120 — IMPAIRING THE ACTIVITY OF AT LEAST ONE SYMPATHETIC NERVE, NERVE FIBER OR NEURON, USING THE PULMONARY ARTERY MANIPULATION DEVICE, TO DENERVATE THE TARGET BLOOD VESSEL, THEREBY IMPROVING THE EJECTION FRACTION OF THE PATIENT

(51) Int. Cl.

| | |
|---|---|
| *A61B 6/03* | (2006.01) |
| *A61B 18/00* | (2006.01) |
| *A61B 18/02* | (2006.01) |
| *A61B 18/08* | (2006.01) |
| *A61B 18/12* | (2006.01) |
| *A61B 18/14* | (2006.01) |
| *A61B 18/18* | (2006.01) |
| *A61B 18/24* | (2006.01) |
| *A61K 31/191* | (2006.01) |
| *A61K 31/343* | (2006.01) |
| *A61K 31/4965* | (2006.01) |
| *A61K 31/4985* | (2006.01) |
| *A61K 31/506* | (2006.01) |
| *A61K 31/519* | (2006.01) |
| *A61K 31/53* | (2006.01) |
| *A61N 2/06* | (2006.01) |
| *A61N 5/10* | (2006.01) |
| *A61N 7/02* | (2006.01) |
| *A61B 6/50* | (2024.01) |
| *A61B 17/00* | (2006.01) |

(52) U.S. Cl.

CPC ........ *A61B 18/082* (2013.01); *A61B 18/1492* (2013.01); *A61B 18/24* (2013.01); *A61K 31/191* (2013.01); *A61K 31/343* (2013.01); *A61K 31/4965* (2013.01); *A61K 31/4985* (2013.01); *A61K 31/506* (2013.01); *A61K 31/519* (2013.01); *A61K 31/53* (2013.01); *A61N 2/06* (2013.01); *A61N 5/1002* (2013.01); *A61N 7/022* (2013.01); *A61B 5/055* (2013.01); *A61B 6/032* (2013.01); *A61B 6/504* (2013.01); *A61B 2017/00292* (2013.01); *A61B 2018/00369* (2013.01); *A61B 2018/00434* (2013.01); *A61B 2018/0212* (2013.01); *A61B 2018/1253* (2013.01); *A61B 2018/126* (2013.01); *A61B 2018/1807* (2013.01); *A61B 2018/1861* (2013.01); *A61N 2007/003* (2013.01); *A61N 2007/0043* (2013.01); *A61N 2007/0078* (2013.01)

(56) References Cited

U.S. PATENT DOCUMENTS

| | | | |
|---|---|---|---|
| 8,377,933 B2 | 2/2013 | Gerber et al. | |
| 8,715,209 B2 * | 5/2014 | Gertner | A61B 8/06 601/3 |
| 9,918,776 B2 | 3/2018 | Chen | |
| 2011/0118725 A1 | 5/2011 | Mayse | |
| 2011/0257562 A1 | 10/2011 | Schaer | |
| 2012/0215106 A1 | 8/2012 | Sverdlik et al. | |
| 2013/0204068 A1 | 8/2013 | Gnanashanmugam et al. | |
| 2014/0180277 A1 | 6/2014 | Chen | |
| 2015/0196357 A1 | 7/2015 | Chen | |
| 2015/0196705 A1 | 7/2015 | Brenneman et al. | |
| 2016/0256216 A1 * | 9/2016 | Chang | A61B 18/1492 |
| 2017/0027645 A1 | 2/2017 | Ben Oren et al. | |
| 2017/0128751 A1 * | 5/2017 | Gilad | A61B 5/021 |
| 2020/0238107 A1 * | 7/2020 | Shabtay | A61K 31/506 |

OTHER PUBLICATIONS

Zhang, Hang, et al. "Pulmonary artery denervation for treatment of a patient with pulmonary hypertension secondary to left heart disease." Pulmonary circulation 6.2 (2016): 240-243. (Year: 2016).*
Oral, H. (2006). Circumferential pulmonary-vein ablation for atrial fibrillation. New England Journal of Medicine, 354(21), 2289-2291. https://doi.org/10.1056/nejmc060884 (Year: 2006).*

Heart failure with preserved Ejection Fraction (HFpEF). Heart Failure with Preserved Ejection Fraction (HFpEF) | Frankel Cardiovascular Center | Michigan Medicine. (Mar. 13, 2017). https://www.umcvc.org/conditions-treatments/heart-failure-preserved-ejection-fraction-hfpef (Year: 2017).*
Hynynen, K., Dennie, J., Zimmer, J. E., Simmons, W. N., Ding Sheng He, Marcus, F. I., & Aguirre, M. (1997). Cylindrical ultrasonic transducers for cardiac catheter ablation. IEEE Transactions on Biomedical Engineering, 44(2), 144-151. https://doi.org/10.1109/10.552244 (Year: 1997).*
Becker, R., & Schoels, W. (2004). Ablation of atrial fibrillation: Energy Sources and Navigation Tools: A Review. Journal of Electrocardiology, 37, 55-62. https://doi.org/10.1016/j.jelectrocard.2004.08.016 (Year: 2004).*
Hsu, L.-F., & Jaïs, P. (2004). Catheter ablation for atrial fibrillation in congestive heart failure. New England Journal of Medicine, 351(23), 2373-2383. https://doi.org/10.1056/nejmoa041018 (Year: 2004).*
Pappone, C., & Augello, G. (2006). A randomized trial of circumferential pulmonary vein ablation versus antiarrhythmic drug therapy in paroxysmal atrial fibrillation. Journal of the American College of Cardiology, 48(11), 2340-2347. https://doi.org/10.1016/j.jacc.2006.08.037 (Year: 2006).*
Khan, M. N., Jaïs, P., & Natale, A. (2008). Pulmonary-vein isolation for atrial fibrillation in patients with heart failure. New England Journal of Medicine, 359(17), 1778-1785. https://doi.org/10.1056/nejmoa0708234 (Year: 2008).*
Anter, E., Jessup, M., & Callans, D. J. (2009). Atrial fibrillation and heart failure. Circulation, 119(18), 2516-2525. https://doi.org/10.1161/circulationaha.108.821306 (Year: 2009).*
Sinelnikov, Y. D., Fjield, T., & Sapozhnikov, O. A. (2009). The mechanism of lesion formation by focused ultrasound ablation catheter for treatment of atrial fibrillation. Acoustical Physics, 55(4-5), 647-656. https://doi.org/10.1134/s1063771009040216 (Year: 2009).*
Ad, N., Henry, L., & Hunt, S. (2011). The impact of surgical ablation in patients with low ejection fraction, heart failure, and atrial fibrillation. European Journal of Cardio-Thoracic Surgery, 40(1), 70-76. https://doi.org/10.1016/j.ejcts.2010.11.016 (Year: 2011).*
Greillier, P., Bawiec, C., Bessière, F., & Lafon, C. (2018). Therapeutic ultrasound for the heart: State of the art. IRBM, 39(4), 227-235. https://doi.org/10.1016/j.irbm.2017.11.004 (Year: 2018).*
Zhang, et al (2016) Pulmonary artery denervation for treatment of a patient with pulmonary hypertension secondary to left heart disease, Pulmonary circulation 6.2: 240-243.
Chen, et al (2013) Percutaneous pulmonary artery denervation completely abolishes experimental pulmonary arterial hypertension in vivo, EuroIntervention 9.2: 269-76.
International Search Report of PCT/IL2018/050316 Completed Jun. 19, 2018; Mailed Jun. 19, 2018 9 pages.
Written Opinion of PCT/IL2018/050316 Completed Jun. 19, 2018; Mailed Jun. 19, 2018 6 pages.
Shao-Liang Chen et al (2013) Pulmonary Artery Denervation to Treat Pulmonary Arterial Hypertension, Journal of the American College of Cardiology, vol. 62, No. 12, pp. 1092.
Kalogeropoulos et al (2011) Pulmonary hypertension and right ventricular function in advanced heart failure, Congestive Heart Failure, 17(4):189-198.
Li, Bao (2013) Cardiovascular Intervention Training Course, published by People's Military Medical Press, ISBN No. 978-7-5091-6440-2, including Section 8 Intra-Aortic Ballon Counterpulsation, pp. 75-77, 26 p. [English Brief Introduction of Contents, English Preface, & English Table of Contents].
Li Yigang (2010), "Clinical Key Technology of Interventional Diagnosis and Treatment of Tachyarrhythmia," published by Scientific and Technical Documents Publishing House, ISBN No. 978-7-5023-6528-8, including Chpt 5 Ultrasonic Ablation Technology, pp. 44-47, 32 pages [English Table of Contents].
Lin Lixue (2007) "Modern Ultrasound In Cardiac Electrophysiology," published by People's Military Medical Press, ISBN No. 978-7-5091-1206-0, including Chpt. 39, Section 2, Ultrasonic Ablation Device, pp. 689-692, 36 pages [English Brief Introduction of Contents & English Table of Contents].

(56) References Cited

OTHER PUBLICATIONS

Natale et al.(2009) "Ventricular Tachycardia/Fibrillation Ablation: the state of the Art based on the VeniceChart International Consensus Document," John Wiley & Sons, p. 264, fig. 14.3, 6 pages.

Zhang et al.(2014) "Perioperative Management of Cardiovascular Diseases," published by People's Medical Publishing House, ISBN No. 987-7-117-18454-0, including Chpt 3 Section 3 Cardiac Ejection and Ventricular Afterload, & Chpt 3, Section 4 Function and Monitoring of Microcirculation pp. 75-79, 20 pages [English Back Cover Synopsis & Table of Contents].

Li, Bao (2013) Cardiovascular Intervention Training Course, published by People's Military Medical Press, ISBN No. 978-7-5091-6440-2, including Section 8 Intra-Aortic Balloon Counterpulsation, pp. 75-77, 31 total p. [English Translation of pp. 75-77, English Brief Introduction of Contents, English Preface, English Table of Contents].

Li Yigang (2010), "Clinical Key Technology of Interventional Diagnosis and Treatment of Tachyarrhythmia," published by Sci-entific and Technical Documents Publishing House, ISBN No. 978-7-5023-6528-8, including Chpt 5, Ultrasound Ablation Technology, pp. 44-47, 36 total p. [English translation of pp. 44-47, English Brief Introduction of Contents, English Preface, & English Table of Contents].

Lin Lixue (2007) "Modern Ultrasound in Cardiac Electrophysiology," published by People's Military Medical Press, ISBN No. 978-7-5091-1206-0, including Chpt. 39, Section 2, Ultrasonic Ablation Device, pp. 689-692, 45 total p. [English translation of pp. 689-692, English Brief Introduction of Contents, English Preface & English Table of Contents].

Zhang et al(2014) "Perioperative Management of Cardiovascular Diseases," published by People's Medical Publishing House, ISBN No. 987-7-117-18454-0, including Chpt 3, Section 3, Cardiac Ejection and Ventricular Afterload, & Chpt 3, Section 4, Function and Monitoring of Microcirculation pp. 75-79, 26 total pages [English translation of pp. 75-79. English Back Cover Synopsis & Table of Contents, English Brief Introduction of Contents, English Preface & English Table of Contents].

* cited by examiner

Figure 1:
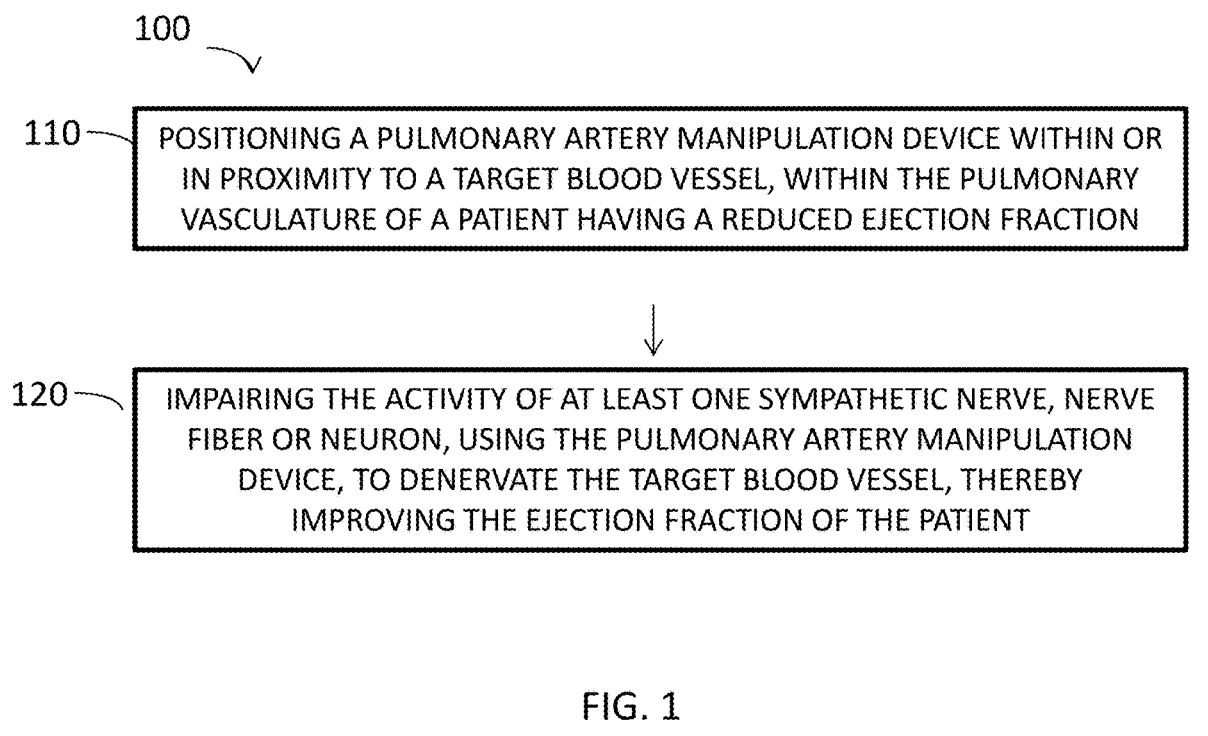

100

110 — POSITIONING A PULMONARY ARTERY MANIPULATION DEVICE WITHIN OR IN PROXIMITY TO A TARGET BLOOD VESSEL, WITHIN THE PULMONARY VASCULATURE OF A PATIENT HAVING A REDUCED EJECTION FRACTION

120 — IMPAIRING THE ACTIVITY OF AT LEAST ONE SYMPATHETIC NERVE, NERVE FIBER OR NEURON, USING THE PULMONARY ARTERY MANIPULATION DEVICE, TO DENERVATE THE TARGET BLOOD VESSEL, THEREBY IMPROVING THE EJECTION FRACTION OF THE PATIENT

METHOD FOR TREATING HEART FAILURE BY IMPROVING EJECTION FRACTION OF A PATIENT

RELATED APPLICATIONS

This application is a National Phase of PCT Patent Application No. PCT/IL2018/050316 having International filing date of Mar. 20, 2018, which claims the benefit of priority of U.S. Provisional Application Nos. 62/473,512, 62/473,545, and 62/473,532 filed on Mar. 20, 2017. The contents of the above applications are all incorporated by reference as if fully set forth herein in their entirety.

TECHNICAL FIELD

The present disclosure relates generally to the field of pulmonary artery denervation for improving a patient's ejection fraction.

BACKGROUND

Ejection fraction refers to the percentage of blood that is pumped out of a filled ventricle with each heartbeat. Left ventricular ejection fraction is a measure of the efficiency of pumping into the systemic circulation, whereas right ventricular ejection fraction is a measure of the efficiency of pumping into the pulmonary circulation. The left ventricle is the heart's main pumping chamber that pumps oxygenated blood through the ascending (upward) aorta to the rest of the body, so ejection fraction is usually measured in the left ventricle (LV). It is calculated by dividing the stroke volume by the end-diastolic volume and is an inherent measure of the pumping efficiency of the heart. Hearts that beat busily but do not succeed in expelling much blood are said to be in heart failure.

A reduced ejection fraction may have multiple causes including cardiomyopathy, damage to the heart as a result of heart attack, heart valve malfunction, long-standing, uncontrolled high blood pressure, high pulmonary ventricle resistance, low distensibility of the arteries, and more.

Ejection fraction is commonly measured by an echocardiogram and serves as a general measure of a person's cardiac function. Other, rarer methods include cardiac catheterization, MRI, CT and nuclear methods such as PET, SPECT and MUGA, in which trace amounts of radioactive material—such as thallium—are injected into the bloodstream and special cameras detect the radioactive material in the blood as it flows through the heart and lungs.

The normal ejection fraction, which demonstrates good ventricular contractility, ranges between 50 to 75%. Reduced ejection fraction (less than 50%) indicates reduced heart pumping efficiency, where the heart does not manage to pump enough blood to the rest of the body and does not meet the body's needs. Patients having a reduced ejection fraction typically suffer from shortness of breath, inability to exercise, swelling of lower limbs, fatigue and weakness, mental confusion and heart arrhythmia. An ejection fraction of 35% or lower is a marker of an increased risk of heart failure, pulmonary congestion, hypertrophy or enlargement of the heart, as well as liver or kidney malfunction.

SUMMARY

Aspects of the disclosure, in some embodiments thereof, relate to methods for improving an ejection fraction of a patient in need thereof.

A moderately reduced ejection fraction can be improved by so called life style changes including low salt diet, fluid management and exercise. However, often such life style changes are not enough. Certain medications can help reduce the heart's workload, increase blood flow, widen vessels or eliminate excess water from the body, all of which may help in treating low ejection fraction. Commonly prescribed medications include: Inotropes (such as digoxin), Angiotensin II receptor blockers and Betablockers. However, some patients do not respond to these medications, leaving cardiac defibrillator implantation as an alternative. There thus remains a need for minimally invasive methods for improving an ejection fraction of a patient.

Advantageously, the methods described herein enable improving the ejection fraction of a patient by denervating the pulmonary vasculature and modulating or reducing sympathetic tone. In aspects thereof, the method relates to positioning an artery manipulation device in or in proximity to a target blood vessel, e.g. within the pulmonary vasculature of a patient having reduced ejection fraction and impairing the activity of at least one sympathetic nerve, nerve fiber or neuron, using the artery manipulation device. The impairment of the nerve, nerve fiber or neuron leads to denervation of the target blood vessel and, as a result thereof, to an improvement in the ejection fraction.

Many patients suffering from a reduced ejection fraction are resistant to most conventional treatments. The method disclosed herein advantageously provides a treatment of patients suffering from a reduced ejection fraction who often have no real treatment option available. Thus, the method provides an efficient treatment solution to patients for whom no efficient treatment is currently available.

According to some embodiments, there is provided a method for improving an ejection fraction of a patient in need thereof, the method comprising: positioning a pulmonary artery manipulation device in a target blood vessel, within the pulmonary vasculature of the patient; and impairing the activity of at least one sympathetic nerve, nerve fiber or neuron, using the pulmonary artery manipulation device, to denervate the target blood vessel, thereby improving the ejection fraction of the patient.

According to some embodiments, the ejection fraction is left ventricle ejection fraction.

According to some embodiments, the ejection fraction is right ventricle ejection fraction.

According to some embodiments, the treatment device comprises an energy transmission device that emits energy selected from the group consisting of monopolar radiofrequency, bipolar radiofrequency, ultrasound, microwave, light, heat, cold radiation, phototherapy, magnetic, electrical, electromagnetic, cryotherapy, plasma, mechanical, chemical, kinetic, potential, nuclear, elastic and hydrodynamic energy, and wherein using the treatment device comprises emitting energy from the catheter.

According to some embodiments, the treatment device comprises an ultrasound transmission device. According to some embodiments, the ultrasound beam is emitted at a frequency of 1-20 Mhz. According to some embodiments, the ultrasound beam is emitted at a frequency of 8-12 Mhz.

According to some embodiments, improving an ejection fraction of the patient comprises decreasing pulmonary vascular resistance (PVR). According to some embodiments, the patient has a pulmonary vascular resistance (PVR) of at least 3 Wood units.

According to some embodiments, the PVR remains essentially unchanged when a pulmonary capillary wedge pressure (PCWP) of the patient is reduced.

According to some embodiments, the PVR remains essentially unchanged when the patient is treated with diuretics, vasodilators, antihypertensive drugs, oxygen, or any combination thereof.

According to some embodiments, denervating the target blood vessel comprises reducing a tone of smooth muscles within a wall of the target blood vessel.

According to some embodiments, impairing the activity of at least one sympathetic nerve, nerve fiber or neuron comprises emitting an ultrasound beam from the pulmonary artery manipulation device. According to some embodiments, the ultrasound beam is an unfocused ultrasound beam.

According to some embodiments, improving an ejection fraction of the patient comprises increasing the patient's pulmonary vascular distensability.

According to some embodiments, improving an ejection fraction of the patient comprises increasing the patient pulmonary vascular compliance.

According to some embodiments, improving an ejection fraction of the patient comprises reducing the patient pulmonary vascular stiffness.

According to some embodiments, improving an ejection fraction of the patient comprises decreasing the patient's pulmonary vascular systolic pressure.

According to some embodiments, improving an ejection fraction of the patient comprises decreasing the patient's right atrial pressure. According to some embodiments, improving an ejection fraction of the patient comprises increasing the patient's cardiac output.

According to some embodiments, improving an ejection fraction of the patient comprises an increase in the patient's cardiac index. According to some embodiments, improving an ejection fraction of the patient comprises an increase in the patient's right atrial pressure. According to some embodiments, improving an ejection fraction of the patient results in an improvement in quality of life (QoL) parameters. According to some embodiments, the herein disclosed denervation treatment may improve proximal pulmonary arteries' compliance which in turn may reduce right ventricular afterload.

According to some embodiments, the method further comprises indicating one or more side effects on an instruction sheet of the method.

According to some embodiments, the one or more side effects is selected from the group consisting of: heart rhythm disturbances, bradycardia; blot clot formation, embolism, ischemia, ischemic events, myocardial infarction, stroke, hemoptysis, hematoma, bruising, bleeding, vascular complications, arterial spasm, arterial stenosis, arterial dissection, perforation, pulmonary perforation, pseudo-aneurysm, AV-fistula; allergic reactions, reduced kidney function, pain, infection, nausea, vomit, fever, death, cardiopulmonary arrest, anxiolytics, pain medication addiction, side effects associated with pain medication used during procedure, anti-vasospasm agents used during procedure, infection, toxicity, adverse hematology, hemorrhage, hemoptysis, pyrogenicity, damage to blood vessel wall or other body structures, pulmonary artery stenosis, nerve damage, spasm, aneurysm formation, aneurism rupture, damage to local anatomical structures, damage to cardiac plexus, damage to esophagus, damage to trachea, damage to lung, damage to vagus, bradycardia, tachycardia, partial vocal cord palsy, haemoptysis, decreased pulmonary function, hypertension, hypo-perfusion, or any combination thereof.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

BRIEF DESCRIPTION OF THE DRAWINGS

Some embodiments of the disclosure are described herein with reference to the accompanying figures. The description, together with the figures, makes apparent to a person having ordinary skill in the art how some embodiments of the disclosure may be practiced. The figures are for illustrative purposes only.

FIG. 1 is an illustrative flowchart of a method for improving an ejection fraction of a patient, according to some embodiments.

DETAILED DESCRIPTION

Figure 2:
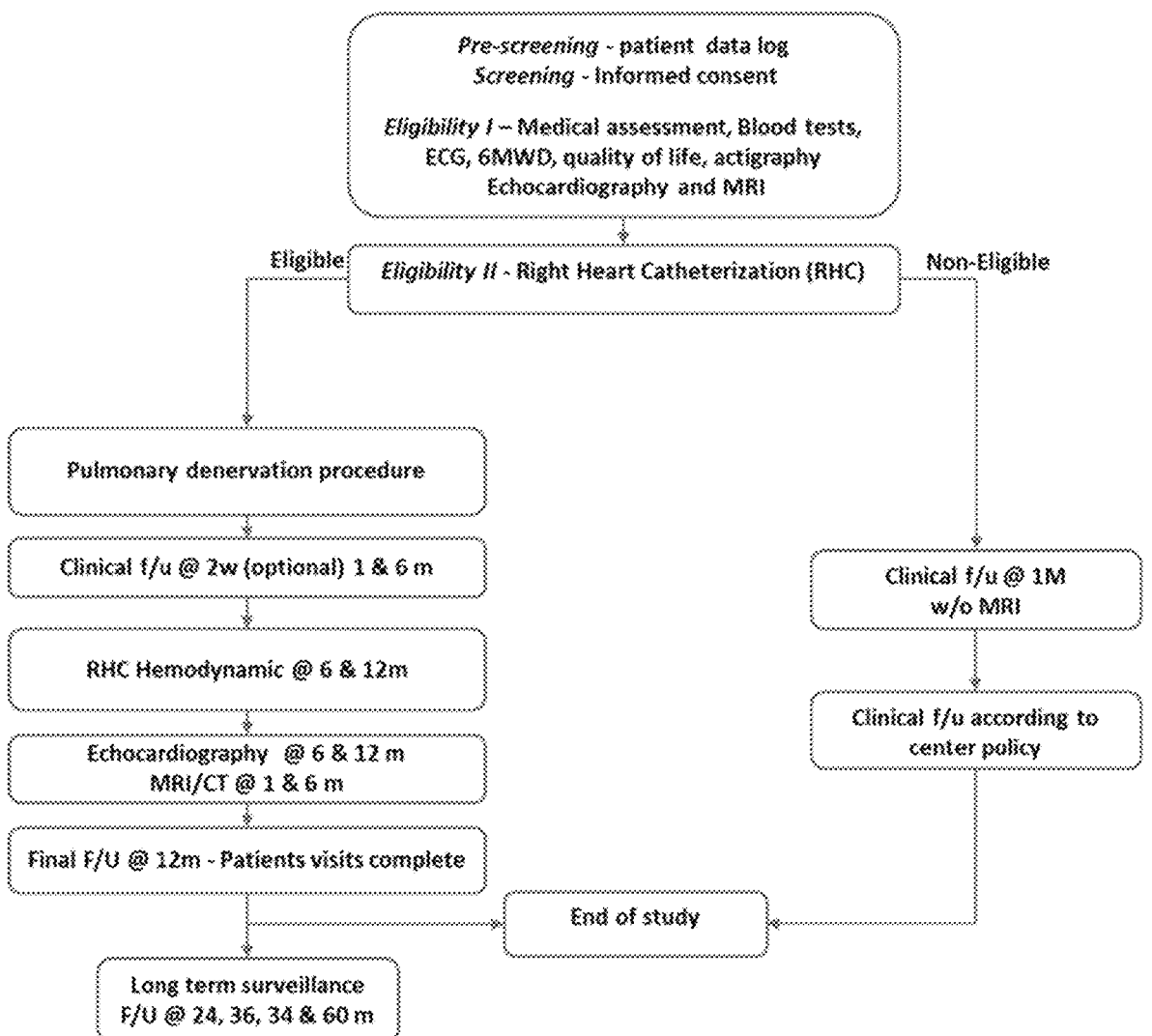
FIG. 2 is an illustrative flowchart of the TROPHY 1 study described in Example 1 herein.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

The present disclosure relates generally to the field of pulmonary artery denervation for improving an ejection fraction, in particular a left ventricular ejection fraction of a patient in need thereof.

According to some embodiments, the method relates to positioning an artery manipulation device in or in proximity to a target blood vessel, e.g. within the pulmonary vasculature of a patient having a reduced ejection fraction and impairing the activity of at least one sympathetic nerve, nerve fiber or neuron, using the artery manipulation device. The impairment of the nerve, nerve fiber or neuron leads to denervation of the target blood vessel and, as a result thereof, to an improvement in the ejection fraction.

According to some embodiments, sympathetic and parasympathetic nerves may be treated, and in other alternative embodiments, parasympathetic nerves alone may be treated. According to some embodiments, nerves may be treated at a neuron-by-neuron level. According to some embodiments, whole nerves may be treated. For the purposes of this disclosure, the phrase "nerves or neurons" may be used to treat one or more whole nerves, one or more nerve fibers, and/or one or more neurons.

According to some embodiments, neurons or nerves will simply be down-regulated. Alternatively, in other embodiments, reducing the sympathetic tone by innervating the pulmonary vasculature may involve partially or completely destroying one or more sympathetic nerves. This process of partial or complete nerve destruction may be referred to herein as "denervating" or "denervation of a structure. For example, in some embodiments, the therapy may involve denervating one or more arteries supplying the lungs, such as, but not limited to, the pulmonary trunk, the left pulmonary artery and/or the right pulmonary artery. According to some embodiments, one or more veins returning blood to the heart from the lungs may be denervated. This method of modulating or reducing thoracic sympathetic tone by denervating the pulmonary vasculature is a unique method for treating impaired ejection fraction.

As used herein the term "artery manipulation device" may refer to any device configured to improve an ejection fraction of a patient. According to some embodiments, the artery manipulation device may include or be an intravascular treatment device. According to some embodiments, the manipulation device may include a device configured to cause pulmonary artery denervation.

According to some embodiments, the manipulation device may include a radiofrequency emitter. According to some embodiments, the pulmonary artery manipulation device may include a modified radiofrequency emitter. According to some embodiments, the pulmonary artery manipulation device may include a laser.

According to some embodiments, the manipulation device may include a catheter and an ultrasound emitter mounted on the catheter. According to some embodiments, the ultrasound beam may be an unfocused ultrasound beam. According to some embodiments, the ultrasound beam may be a high intensity focused ultrasound beam. According to some embodiments, the ultrasound beam may be a low frequency ultrasound beam. According to some embodiments, the ultrasound beam may be emitted at a frequency of 1-50 MHz, 5-15 MHz, 8-12 MHz, or any other suitable frequency. Each possibility is a separate embodiment.

According to some embodiments, the catheter may have a length of 100-150 cm, such as, but not limited to, about 120 cm.

In some embodiments, a duration of treatment at each site ranges between, for example, 10-80 seconds, such as 20 seconds, 40 seconds, 70 seconds or intermediate, shorter or longer time periods.

In some embodiments, the applied ultrasound intensity ranges between, for example, 30-70 W/cm^2, such as 40 W/cm^2, 50 W/cm^2, 60 W/cm^2 or intermediate, higher or lower intensities.

According to some embodiments the method includes positioning a pulmonary artery manipulation device within or in proximity to a target blood vessel.

As used herein, the term "proximity" may refer to the manipulation device touching the target blood vessel or being distanced 1 mm, 2 mm, 5 mm, 1 cm or more from the wall of the target blood vessel. Each possibility is a separate embodiment.

According to some embodiments, positioning a treatment device within or in proximity to a target blood vessel may impair the activity of at least one sympathetic nerve, nerve fiber or neuron. According to some embodiments, impairing the activity of at least one sympathetic nerve, nerve fiber or neuron may denervate the target blood vessel, thereby improving the ejection fraction of the patient.

In some embodiments, one or more of the following safety measures are taken before, after and/or during treatment: in some embodiments, the catheter is used for treating a single patient only; in some embodiments, re-sterilization and/or re-use of the catheter is avoided; in some embodiments, the catheter is used only with its compatible console; in some embodiments, the method is performed while avoiding applying direct pressure onto the distancing device and/or ultrasonic transducers of the device during preparation; in some embodiments, during treatment, if the distancing device is open, manipulation and/or retraction of the catheter are avoided; in some embodiments, during energy delivery, the catheter is not moved; in some embodiments, for example in cases in which additional electrical devices are used during operation in addition to the catheter, the system is disconnected by unplugging the power cable and/or by withdrawing the catheter; in some embodiments, in the event the distancing device malfunctions, the distancing device can be retracted along with the catheter and/or along with the guide sheath; in some cases in which fluoroscopy is performed, care should be taken to avoid excessive exposure of the patient to contrast agents; in some embodiments, before treatment, a patient is provided with a systemic anticoagulant. Optionally, an activated clotting time (ACT) is monitored during treatment. In some cases, an ACT of at least 250 seconds should be maintained. In some embodiments, use of the catheter and/or console is allowed only for trained, qualified medical personnel (e.g. right heart catheterization experts); in some embodiments, during the procedure, Echocardiography and equipment for diagnosis and immediate therapeutic actions for pericardial tamponade should be made available; in some embodiments, care should be taken to avoid using electro-medical energy sources in the presence of flammable detergents, anesthetics, nitrous oxide (N2O), or oxygen that are not controlled in a closed-circuit environment; in some embodiments, use of the system is permitted only following completion of training; in some cases in which tissue dissection or perforation of the pulmonary artery have occurred, care should be taken when introducing the catheter; in some embodiments, the catheter and/or other accessories (e.g. distancing device) are to be disposed of according to established hospital protocols of biohazardous waste disposal; in some embodiments, only predefined intended target areas are treated; in some embodiments, powered and/or automatic contrast injection devices may be used before and/or during the procedure; optionally, specified settings for flow injection and/or contrast agent delivery are taken into consideration; in some embodiments, water ingress into the console should be avoided; in some cases, if the patient suffers from excessive pain during treatment, analgesia and/or sedation should be considered; in some cases, if radiography is used, radiation hazards should be handled.

According to some embodiments, the method further comprises indicating one or more side effect on the instruction to use. According to some embodiments, the side effects may be selected from the group consisting of: heart rhythm disturbances including bradycardia; formation of blood clot and/or embolism, possibly resulting in ischemic events such as myocardial infarction, stroke, hemoptysis; hematoma, bruising, bleeding; vascular complications including arterial spasm, arterial stenosis, arterial dissection, perforation, pulmonary perforation, pseudo-aneurysm, AV-fistula; complications associated with the contrast agent used during the procedure, e.g., serious allergic reaction or reduced kidney function; pain; infection; nausea or vomiting; fever; death; cardiopulmonary arrest; risks associated with contrast agents, narcotics, anxiolytics, other pain medications and anti-vasospasm agents used during the procedure; biological hazards: risks of infection, toxicity, adverse hematology, allergy, hemorrhage, hemoptysis, pain and pyrogenicity; damage to the blood vessel wall or other body structures from the delivery of energy, e.g., pulmonary artery stenosis, nerve damage, spasm, aneurysm formation or rupture; unintended/unexpected damage to local anatomical structures such as the cardiac plexus, esophagus, trachea, lung or vagus, leading to bradycardia, tachycardia, partial vocal cord palsy or Haemoptysis; decreased pulmonary function; hypertension; hypo-perfusion, or any combination thereof. Each possibility is a separate embodiment.

As referred to herein, the terms "patient" and "subject" may interchangeably be used and may relate to a subject having a reduced ejection fraction.

As used herein, the term "ejection fraction" refers to a percentage of blood that is pumped out of a filled ventricle with each heartbeat. According to some embodiments, the ejection fraction may be left ventricular ejection fraction. According to some embodiments, the ejection fraction may be right ventricular ejection fraction.

According to some embodiments, a reduced ejection fraction may be defined as an ejection fraction below 55 percent, below 50 percent, or below 35 percent. Each possibility is a separate embodiment.

According to some embodiments, the patient having a reduced ejection fraction may include patients with an increased trans-pulmonary gradient (TPG) and/or an elevated pulmonary vascular resistance (PVR). As used herein, the term "trans-pulmonary gradient" may refer to the difference between mean pulmonary arterial pressure (mPAP) and left atrial pressure (PLA; commonly estimated by pulmonary capillary wedge pressure: PCWP). According to some embodiments, an increased TPG may refer to an mPAP-PCWP that exceeds 12-15 mmHg. According to some embodiments, an elevated PVR may refer to a PVR above 2 Wood units, above 2.5 Wood units, above 3 Wood units or above 3.5 Wood units.

According to some embodiments, improving the ejection fraction may include increasing an ejection fraction by 5 percent, or by 10 percent.

According to some embodiments, improving the ejection fraction may include decreasing the pulmonary vascular resistance (PVR) in at least one artery of the pulmonary vasculature.

According to some embodiments, the PVR of the patient is at least 2.5 Wood units. According to some embodiments, the PVR of the patient remains essentially unchanged when a pulmonary capillary wedge pressure (PCWP) of the patient is reduced. According to some embodiments, the PVR of the patient remains essentially unchanged when the patient is treated with a diuretic and/or a vasodilator.

According to some embodiments, impairing the activity of at least one nerve, nerve fiber or neuron may include providing monopolar radiofrequency, bipolar radiofrequency, ultrasound, light, heat, cold radiation, microwave radiation, phototherapy, magnetic therapy, electromagnetic radiation, electrotherapy, cryotherapy, plasma therapy, mechanical manipulation, kinetic therapy, nuclear therapy, elastic and hydrodynamic energy.

According to some embodiments, impairing the activity of at least one nerve, nerve fiber or neuron may include emitting an ultrasound beam from the pulmonary artery manipulation device.

According to some embodiments, improving an ejection fraction of the patient comprises an increase in the patient's cardiac index. As used herein, the term "cardiac index" and "CI" are interchangeable and refer to the hemodynamic parameter that relates the cardiac output (CO) from left ventricle in one minute to body surface area (BSA), thus relating heart performance to the size of the individual. The unit of measurement is liters per minute per square meter (L/min/m2). The normal range of cardiac index at rest is 2.6-4.2 L/min/m2.

According to some embodiments, improving an ejection fraction of the patient comprises an increase in the patient's right atrial pressure. As used herein, the terms "right atrial pressure", "RA Pressure" and "RAP" may interchangeably refer to the blood pressure in the right atrium of the heart. The RAP reflects the amount of blood returning to the heart and the ability of the heart to pump the blood into the arterial system. The normal range of RAP is 2-6 mmHg or below 8 mmHg.

According to some embodiments, improving an ejection fraction of the patient results in an improvement in quality of life (QoL) parameters. Non-limiting examples of suitable QoL parameters include: quality of life (QoL) score (the patient's subjective assessment of his/her quality of life); 6-minute walking distance (6MWD), actimetry (daily activity).

According to some embodiments, the herein disclosed denervation treatment may improve proximal pulmonary arteries' compliance which in turn may reduce right ventricular afterload.

Reference is now made to FIG. 1 which is an illustrative flowchart of a method 100 for improving an ejection fraction of a patient, according to some embodiments. In step 110 a pulmonary artery manipulation device is positioned in a target blood vessel, within the pulmonary vasculature of a patient having a reduced ejection fraction. According to some embodiments, the pulmonary artery manipulation device may be an ultrasound transmission device, as essentially described herein. In step 120 the activity of at least one sympathetic nerve is impaired in order to denervate the target blood vessel and thereby improve the ejection fraction of the patient.

EXAMPLES

Example 1—Pulmonary Artery Denervation Improves Ejection Fraction in Human Study (TROPHY 1)

The TROPHY 1 study is a clinical evaluation of the Therapeutic Intra-Vascular Ultrasound (TIVUS™) System for pulmonary artery denervation in patients with reduced ejection fraction. The outline of the study is shown in the flowchart of FIG. 2. 15 patients were enrolled in the study, and initial results have been obtained for three patients. The study was aimed at assessing the safety, performance and initial effectiveness of pulmonary denervation on ejection fraction directly and through the evaluation of heart function, exercise tolerance (6 minutes walking distance) and quality of life questionnaires. The pulmonary denervation was performed (in patients eligible according to study criteria), in the right, left and main pulmonary arteries according to manufacturer's instructions. The duration of the denervation procedure was 20-30 minutes on average, and the usability feedback from the operators was excellent. The number of denervation sites for each patient varied between 6 and 16, according to the specific patient anatomy. Following the procedure, patients were evaluated, according to the study protocol, 1, 4, 8 and 12 months post procedure. Patient ejection fraction was measured using MRI before and 1 and 12 months after the procedure. Initial results (n=3), from the 1 month follow-up, demonstrate an average increase of 28% in the ejection fraction in both right and left ventricles following the pulmonary denervation, as set forth in table 1 below.

TABLE 1

| MRI based ejection fraction before and 1 month after pulmonary denervation | | | |
| --- | --- | --- | --- |
| Patient | Ejection Fraction Pre-Procedure (%) | Ejection Fraction 1 M Post-Procedure (%) | LV/RV |
| 002-001 | 23 | 31 | RV |
| 001-001 | 11 | 16 | RV |
| 001-001 | 48 | 60 | LV |
| 001-002 | 48 | 52 | RV |

At the 4-month follow-up, all subjective and objective measurable parameters were improved. FIG. 3A-FIG. 3D shows average changes in hemodynamic parameters 4 months after the denervation procedure (Mean/Standard Err; Wilcoxon test 4M Vs Baseline; n=11 (Patient 001-004 excluded)).

Figure 3A:
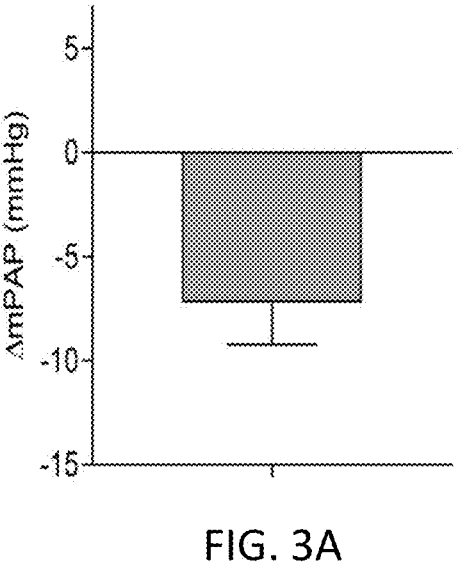
FIG. 3A shows average changes in mean Pulmonary Artery Pressure (mPAP) 4 months after the denervation procedure (Mean/Standard Err; Wilcoxon test 4M Vs Baseline; n=11 (Patient 001-004 excluded))
Figure 3B:
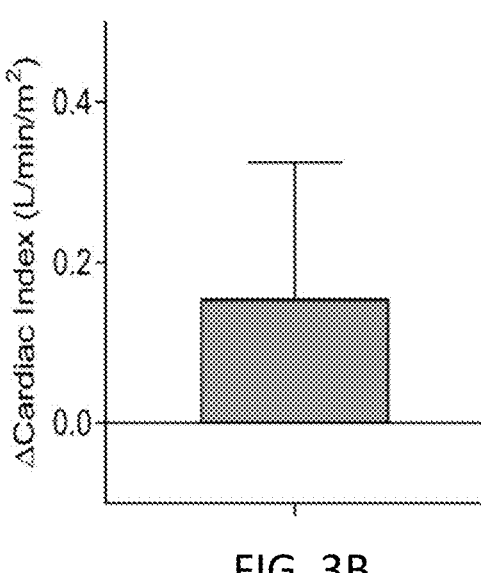
FIG. 3B shows average changes in cardiac index 4 months after the denervation procedure (Mean/Standard Err; Wilcoxon test 4M Vs Baseline; n=11 (Patient 001-004 excluded))
Figure 3C:
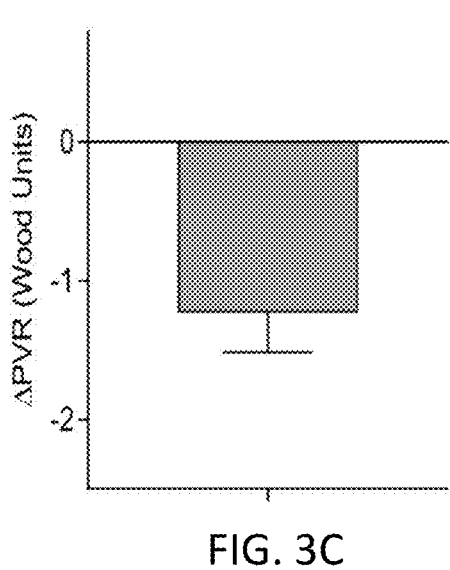
FIG. 3C shows average changes in pulmonary vascular resistance (PVR) 4 months after the denervation procedure (Mean/Standard Err; Wilcoxon test 4M Vs Baseline; n=11 (Patient 001-004 excluded))
Figure 3D:
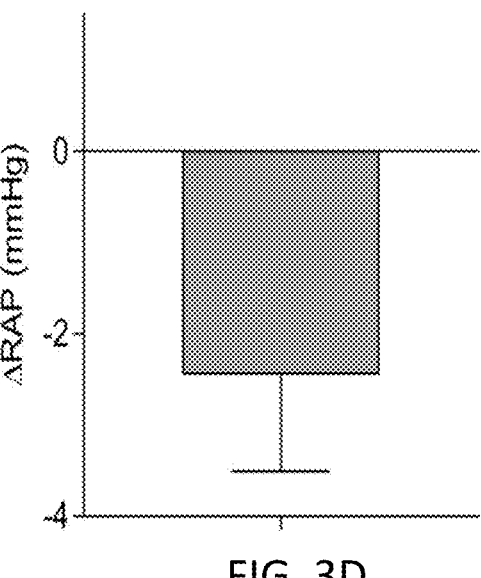
FIG. 3D shows average changes in right arterial pressure (RAP) 4 months after the denervation procedure (Mean/Standard Err; Wilcoxon test 4M Vs Baseline; n=11 (Patient 001-004 excluded))

Advantageously, the mean Pulmonary Artery Pressure (mPAP) was reduced by 13.5% (mean±sd=−7.2±6.6, p=0.010), as shown in FIG. 3A; the cardiac index increased by 2% (mean±sd=0.15±0.52, p=0.695), as seen in FIG. 3B; pulmonary vascular resistance (PVR) reduced by 15.0% (mean±sd=−1.32±0.98, p=0.003), as seen in FIG. 3C; and the right arterial pressure reduced by 20.5% (mean±sd=−2.45±3.5, p=0.053), as seen in FIG. 3D. These results suggest that Therapeutic Intra-Vascular Ultrasound treatment can improve proximal Pulmonary Arteries compliance which in turn reduces right ventricular afterload.

Figures 4A, 4B:
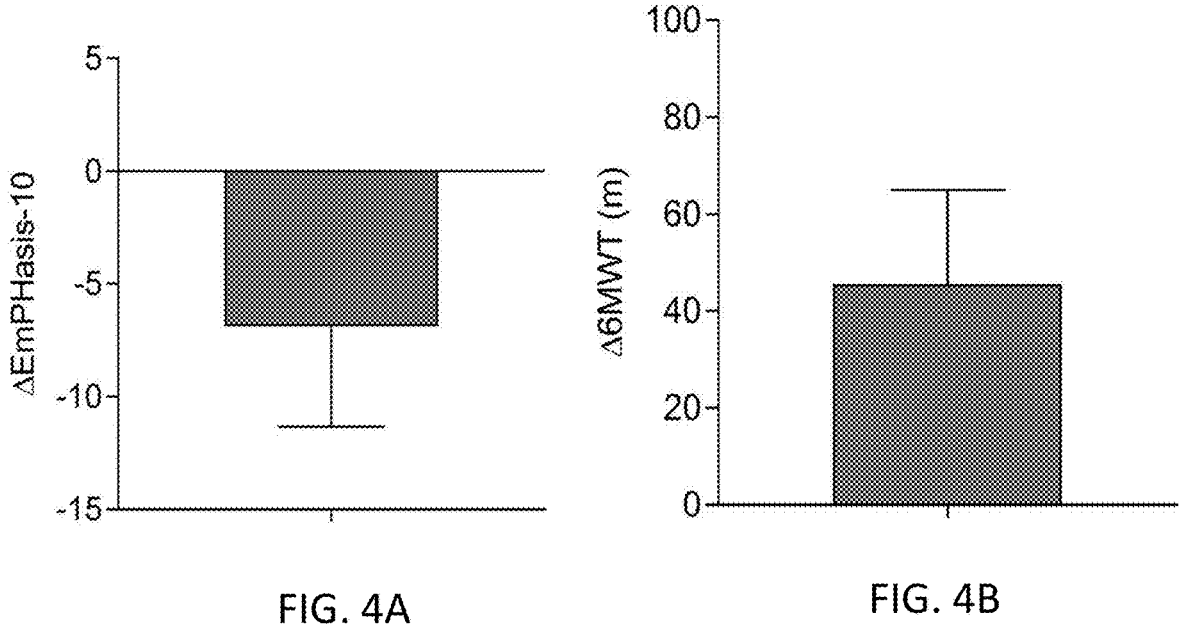
FIG. 4A shows average changes in quality-of-life (QoL) score, 4 months after the denervation procedure (Mean/Standard Err; Wilcoxon test 4M Vs Baseline; n=11 (Patient 001-004 excluded))
FIG. 4B shows average changes in 6-minute walking distance (6MWD), 4 months after the denervation procedure (Mean/Standard Err; Wilcoxon test 4M Vs Baseline; n=11 (Patient 001-004 excluded))
Figure 4C:
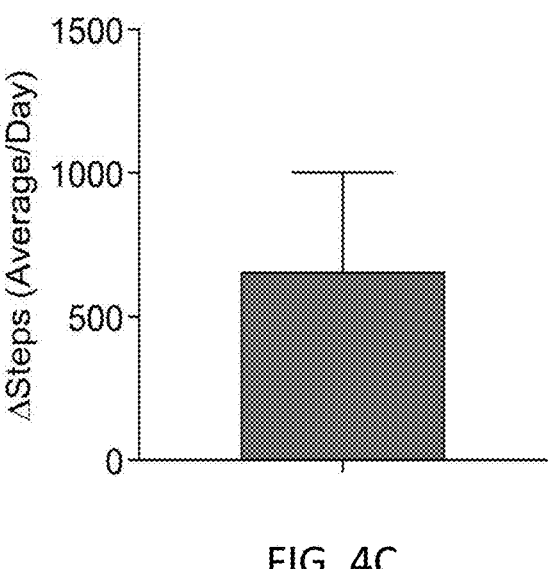
FIG. 4C shows average changes in daily activity (actimetry), 4 months after the denervation procedure (Mean/Standard Err; Wilcoxon test 4M Vs Baseline; n=11 (Patient 001-004 excluded)).

FIG. 4A-FIG. 4C shows average changes in quality-of-life (QoL) parameters, 4 months after the denervation procedure (Mean/Standard Err; Wilcoxon test 4M Vs Baseline; n=11 (Patient 001-004 excluded)).

Advantageously, a positive change in the quality of life score (QoL) indicated by a 21% reduction in the EmPHasis-10 was observed (mean±sd=−6.9±14, p=0.275), as shown in FIG. 4A. Moreover, a 40 meter (21%) improvement in the 6-minute walking distance (6MWD) was like wise observed (mean±sd=45.5±64.6, p=0.065), as seen from FIG. 4B, as well as a 12% increase in daily activity (actimetry) (mean±sd=584±883, p=0.141) as seen from FIG. 4C.

The examples described above are non-limiting examples and are not intended to limit the scope of the disclosure. The described examples may comprise different features, not all of which are required in all embodiments of the disclosure.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising", when used in this specification, specify the presence of stated features, integers, steps, operations, elements, or components, but do not preclude or rule out the presence or addition of one or more other features, integers, steps, operations, elements, components, or groups thereof.

In the description and claims of the application, each of the words "comprise" "include" and "have", and forms thereof, are not necessarily limited to members in a list with which the words may be associated.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

The invention claimed is:

1. A method for improving an ejection fraction of a patient in need thereof, the method comprising:
   positioning a treatment device in a target arterial blood vessel, within a pulmonary vasculature of the patient; wherein the patient is diagnosed as having an ejection fraction of below 50%; and
   impairing an activity of at least one sympathetic nerve, nerve fiber or neuron, using the treatment device, to denervate the target arterial blood vessel, wherein the impairing improves the ejection fraction of the patient, wherein the treatment device comprises an ultrasound transmission device configured to emit an ultrasound beam at a frequency of 1-20 MHz.

2. The method of claim 1, wherein the ejection fraction is left ventricle ejection fraction.

3. The method of claim 1, wherein the ejection fraction is right ventricle ejection fraction.

4. The method of claim 1, wherein the ultrasound beam is emitted at a frequency of 8-12 MHz.

5. The method of claim 1, wherein impairing the activity of at least one sympathetic nerve, nerve fiber or neuron comprises emitting an ultrasound beam from the treatment device.

6. The method of claim 5, wherein the ultrasound beam is an unfocused ultrasound beam.

7. The method of claim 1, further comprising indicating one or more side effects.

8. The method of claim 7, wherein the one or more side effects is selected from the group consisting of: heart rhythm disturbances, bradycardia, blot clot formation, embolism, ischemia, ischemic events, myocardial infarction, stroke, hemoptysis, hematoma, bruising, bleeding, vascular complications, arterial spasm, arterial stenosis, arterial dissection, perforation, pulmonary perforation, pseudo-aneurysm, AV-fistula, allergic reactions, reduced kidney function, pain, infection, nausea, vomit, fever, death, cardiopulmonary arrest, anxiolytics, pain medication addiction, side effects associated with pain medication used during procedure, anti-vasospasm agents used during a procedure, infection, toxicity, adverse hematology, hemorrhage, hemoptysis, pyrogenicity, damage to blood vessel wall or other body structures, pulmonary artery stenosis, nerve damage, spasm, aneurysm formation, aneurism rupture, damage to local anatomical structures, damage to cardiac plexus, damage to esophagus, damage to trachea, damage to lung, damage to vagus, bradycardia, tachycardia, partial vocal cord palsy, haemoptysis, decreased pulmonary function, hypertension, hypo-perfusion, or any combination thereof.

9. The method of claim 1, wherein the patient has an ejection fraction below 35%.

10. The method of claim 1, wherein the target arterial blood vessel is one of a pulmonary trunk, a left pulmonary artery, and a right pulmonary artery.

11. The method of claim 1, wherein the ultrasound beam has an intensity in a range of 30 Watts (W)/centimeter (cm) 2 to 70 W/cm$^2$.

\* \* \* \* \*